US00PP30761P3

(12) United States Plant Patent
Wood

(10) Patent No.: US PP30,761 P3
(45) Date of Patent: Jul. 30, 2019

(54) ***THUJA* PLANT NAMED 'SMNTOBAB'**

(50) Latin Name: *Thuja occidentalis*
Varietal Denomination: SMNTOBAB

(71) Applicant: Timothy Wood, Spring Lake, MI (US)

(72) Inventor: Timothy Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,610

(22) Filed: Nov. 30, 2017

(65) Prior Publication Data

US 2019/0166744 P1 May 30, 2019

(51) Int. Cl.
*A01H 7/00* (2006.01)

(52) U.S. Cl.
USPC ..... Plt./213

(58) Field of Classification Search
USPC ..... Plt./213

CPC ... A01H 7/00; A01H 5/00; A01H 5/02; A01H 5/025; A01H 6/14

See application file for complete search history.

(56) References Cited

PUBLICATIONS

Spring Meadow Nursery Flowering Shrubs Starter Plants Catalog and Shrub Reference 2017-2018,retrieved on Nov. 5, 2018, retrieved from the Internet at https://springmeadownursery.com/files/resource_files/2017-18_SMM_Catalog_1-50.pdf, pp. 1-9, 24 and 88. (Year: 2017).*

* cited by examiner

*Primary Examiner* — June Hwu
(74) *Attorney, Agent, or Firm* — Cassandra Bright

(57) ABSTRACT

A new and distinct *Thuja* cultivar named 'SMNTOBAB' is disclosed, characterized by a dwarf plant habit with rapid growth. Plants have distinctive ball-shaped plant habit well-suited for container cultivation. Plants are very cold hardy. The new cultivar is a *Thuja*, suitable for ornamental garden purposes.

2 Drawing Sheets

Latin name of the genus and species: *Thuja occidentalis*.
Variety denomination: 'SMNTOBAB'.

BACKGROUND OF THE INVENTION

The new cultivar, hereinafter referred to as 'SMNTOBAB', was discovered by the inventor, Timothy Wood, in a commercial nursery in Grand Haven, Mich. This new discovery is the result of an open-pollination of the seed parent *Thuja occidentalis* 'Brandon' (unpatented) with unidentified pollen parents conducted during 2003.

The new variety was first identified as an interesting new plant during 2007 at the same commercial nursery in Grand Haven, Mich. After identifying the new variety as a potentially interesting selection, the inventor first organized propagation of 'SMNTOBAB' by softwood cuttings at the same commercial nursery during 2007. The inventor continued controlled testing and propagation, assessing stability of the unique characteristics of this variety. At least five generations have been reproduced and have shown that the unique features of this cultivar are stable and reproduced true to type.

SUMMARY OF THE INVENTION

The cultivar 'SMNTOBAB' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SMNTOBAB' These characteristics in combination distinguish 'SMNTOBAB' as a new and distinct *Thuja* cultivar:

1. Fast growing dwarf plant.
2. Very cold hardy.
3. Good container plant.

COMPARISON TO PARENT VARIETY

'SMNTOBAB' is similar in most horticultural characteristics to the parent variety *Thuja occidentalis* 'Brandon'. Plants of the new cultivar 'SMNTOBAB' however, differ in the following way:

1. New cultivar is a dwarf ball shaped plant; parent is a taller, upright plant.

COMMERCIAL COMPARISON

*Thuja* 'SMNTOBAB' can be compared to the commercial variety *Thuja* 'Anna Von Vloten', U.S. Plant Pat. No. 25,868. Plants are similar in most horticultural characteristics, however, plants of the new variety differ in the following:

1. 'SMNTOBAB' has darker green foliage, this comparator has lime green foliage.
2. 'SMNTOBAB' is more compact in plant habit than this comparator.

BRIEF DESCRIPTION OF THE PHOTOGRAPHS

Figure 1:
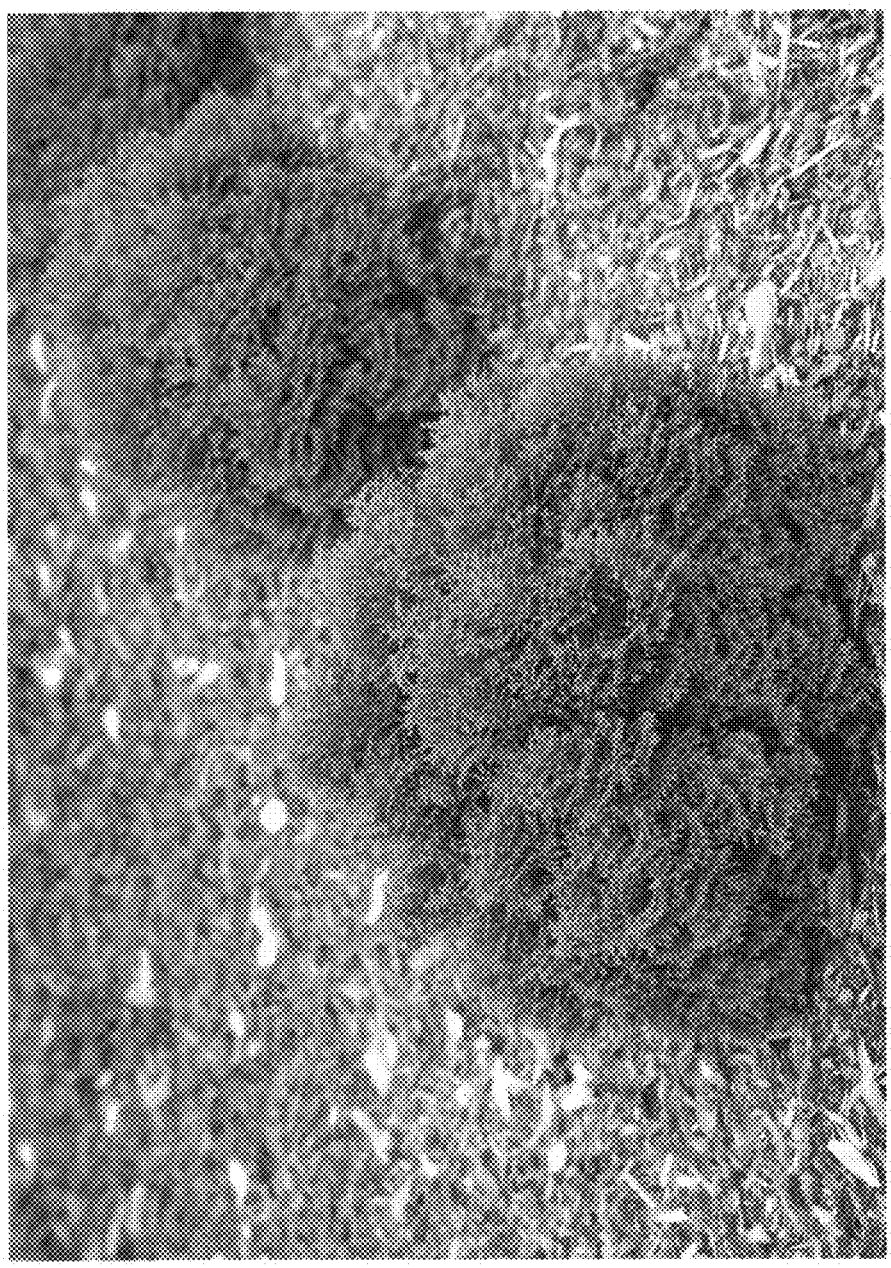

The accompanying photograph in FIG. 1 illustrates in full color a typical plant of 'SMNTOBAB' grown outdoors in Grand Haven, Mich. The plant is approximately 2 years old, and is shown in the ground.

Figure 2:
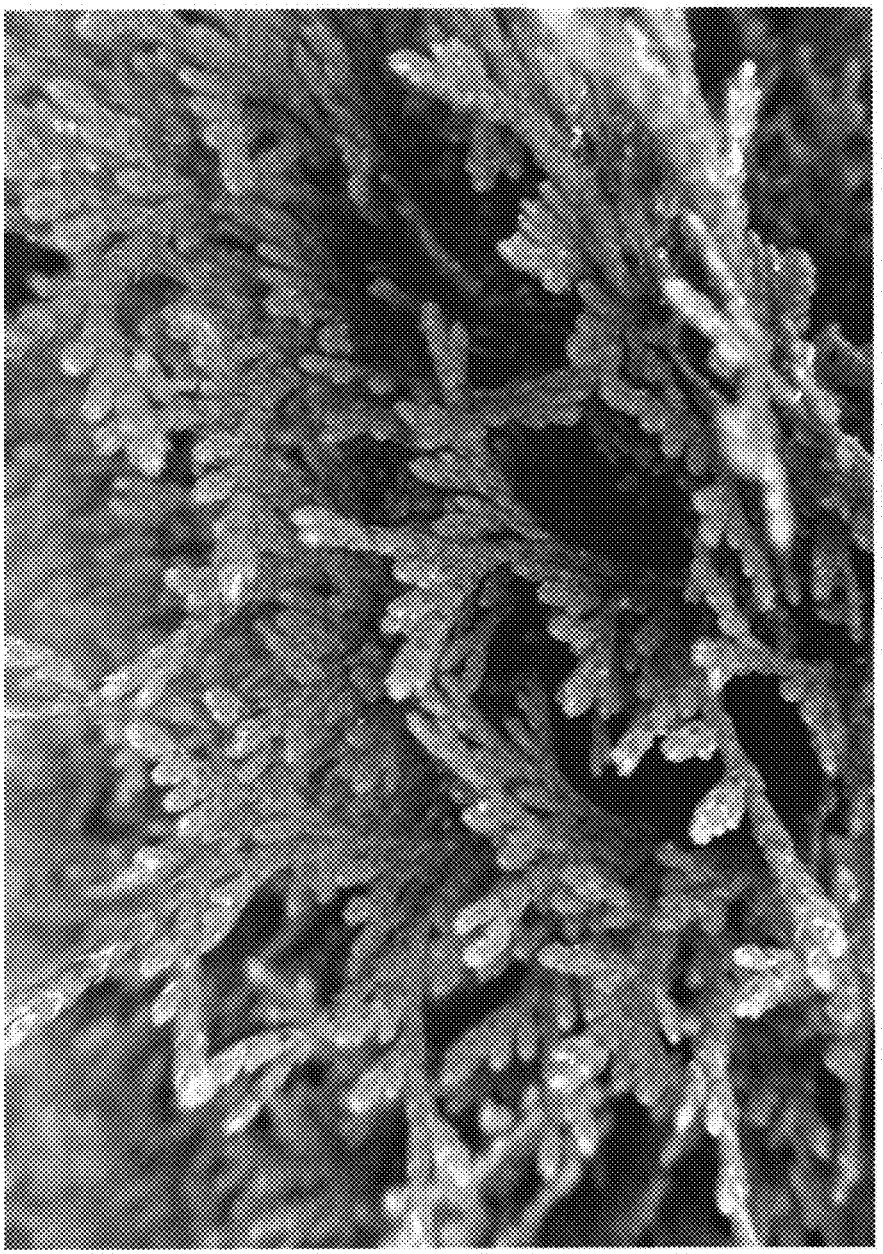

FIG. 2 shows a close up of typical foliage of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'SMNTOBAB' plants grown outdoors in Grand Haven Mich. Plants are approximately 2-3 years old, in a 3 gallon nursery container. Measurements and numerical values represent averages of typical plant types.

Botanical classification: *Thuja occidentalis* 'SMNTOBAB'.

PROPAGATION

Time to rooting: 60 to 90 days at approximately 40-50° F.

Root description: Thick to fine, fibrous and fleshy, freely branching. Colored white and tan, not accurately measured with The R.H.S. Chart.

PLANT

Growth habit: Dwarf, ball shaped.

Height: 37 cm.

Plant spread: 55 cm.

Typical growth rate: Rapid. Branchlets growing on average 8 to 15 cm in a season, depending upon maturity and environmental conditions.

Pinching required: Yes, minimal pinching forms a more round plant.

Branching characteristics: Outwards and upwards.

Length of lateral branches: 23 cm.

Average number of lateral branches: About 100.

Diameter of lateral branches: 5 mm.

Lateral branch shape in cross section: Oval.

Lateral branch texture: Rough, somewhat scaly.

Lateral branch color: Brown N200C.

Lateral branch strength: Very strong.

*Branchlet orientation*.—Horizontal, or nearly horizontal, (75°-90° from center).

Internode length: 1 cm.

Trunk bark:

*Color*.—Near RHS Brown N200B.

*Texture*.—Rough, somewhat scaly.

FOLIAGE

Leaf:

*Arrangement*.—Alternate, overlapping scales.

*Shape*.—Scales.

*Average length*.—1.5 mm.

*Average width*.—1 mm.

*Apex*.—Acuminate.

*Base*.—Truncate.

*Margin*.—Entire.

*Texture of top surface*.—Waxy.

*Texture of bottom surface*.—Waxy.

*Color*.—Young foliage upper side: Green 139B. Young foliage under side: Green 143A. Mature foliage upper side: Green 139B. Mature foliage under side: Green 143A.

*Venation*.—Indistinguishable from leaf blade.

*Fragrance*.—None.

FLOWER

Flowering not observed.

OTHER CHARACTERISTICS

Disease and pest resistance: Neither resistance nor susceptibility observed.

Drought tolerance: No tolerance for drought.

Temperature tolerance: −29° C. to 39° C.

What is claimed is:

1. A new and distinct cultivar of *Thuja* plant named 'SMNTOBAB' as herein illustrated and described.

* * * * *